United States Patent
Divi et al.

(10) Patent No.: US 11,400,074 B1
(45) Date of Patent: Aug. 2, 2022

(54) ENZYMATIC PROCESS FOR THE PREPARATION OF (2S)-2-[(4R)-2-OXO-4-PROPYL-PYRROLIDIN-1-YL]BUTYRIC ACID AND ITS CONVERSION INTO BRIVARACETAM

(71) Applicant: Divi's Laboratories Ltd., Hyderabad (IN)

(72) Inventors: Satchandra Kiran Divi, Hyderabad (IN); Mysore Aswathanarayana Rao, Hyderabad (IN); Shaik Nowshuddin, Hyderabad (IN)

(73) Assignee: Divi's Laboratories Ltd., Hyderabad (IN)

( * ) Notice: Subject to any disclaimer, the term of this patent is extended or adjusted under 35 U.S.C. 154(b) by 0 days.

(21) Appl. No.: 17/183,436

(22) Filed: Feb. 24, 2021

(30) Foreign Application Priority Data

Feb. 1, 2021 (IN) .............................. 202141004400

(51) Int. Cl.
*A61K 31/4015* (2006.01)
(52) U.S. Cl.
CPC .............................. *A61K 31/4015* (2013.01)
(58) Field of Classification Search
CPC ................................................ A61K 31/4015
See application file for complete search history.

(56) References Cited

U.S. PATENT DOCUMENTS 8,338,621 B2  12/2012  Surtees et al.
8,957,226 B2  2/2015  Ates et al.

FOREIGN PATENT DOCUMENTS

WO  01/62726 A2  8/2001

OTHER PUBLICATIONS

Ciceri et al. "A New Chemoenzymatic Synthesis of the Chiral Key Intermediate of the Antiepileptic Brivaracetam." Molecules 23, No. 9 (2018): 2206.
Fuchs et al. "Asymmetric Amination of α-Chiral Aliphatic Aldehydes via Dynamic Kinetic Resolution to Access Stereocomplementary Brivaracetam and Pregabalin Precursors." Advanced Synthesis & Catalysis 360, No. 4 (2018): 768-778.
Kenda at al. (2004). Discovery of 4-substituted pyrrolidone butanamides as new agents with significant antiepileptic activity, Journal of Medicinal Chemistry, 47(3), 530-549.
Ma et al. (2003). Mild method for ullmann coupling reaction of amines and aryl halides, Organic Letters, 5(14) 2453-2455.
Reznikov et al. "Nitroalkenes in the Ni (II) Catalyzed Asymmetric Michael Addition. Convenient Route to the Key Intermediate of Brivaracetam." Helvetica Chimica Acta 101, No. 12 (2018): e1800170.
Schule et al. "A biocatalytic route to the novel antiepileptic drug Brivaracetam " Organic Process Research & Development 20, No. 9 (2016): 1566-1575.

*Primary Examiner* — Brandon J Fetterolf
*Assistant Examiner* — Lauren Q. Wells
(74) *Attorney, Agent, or Firm* — Caesar Rivise, PC

(57) ABSTRACT

A process for the preparation of Brivaracetam, an anti-convulsion drug, is provided comprising enzymatic conversion of (2RS)-2-[(4R)-2-oxo-4-propyl-pyrrolidin-1-yl] butyric acid methyl ester selectively into (2S)-2-[(4R)-2-oxo-4-propyl-pyrrolidin-1-yl] butyric acid having high chiral purity, using protease from *Bacillus licheniformis*. Converting the chirally pure acid into amide results in Brivaracetam.

4 Claims, No Drawings

ENZYMATIC PROCESS FOR THE PREPARATION OF (2S)-2-[(4R)-2-OXO-4-PROPYL-PYRROLIDIN-1-YL]BUTYRIC ACID AND ITS CONVERSION INTO BRIVARACETAM

BACKGROUND OF THE INVENTION

Field of Invention

The present invention relates to an improved process for the preparation of Brivaracetam, a drug useful in treating epilepsy and related central nervous system disorders.

Brivaracetam is chemically (2S)-2-[(4R)-2-oxo-4-propyl-pyrrolidin-1-yl] butanamide (I), having the structure:

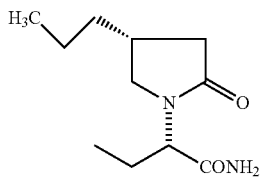

Brivaracetam and a process for its preparation was first disclosed in WO 01/62726 (Scheme 1). The 5-hydroxy-4-propyl-furan-2-one is condensed with (S)-2-aminobutyramide through reductive amination followed by further reduction to give racemic Brivaracetam. The racemic Brivaracetam is resolved using chiral chromatography.

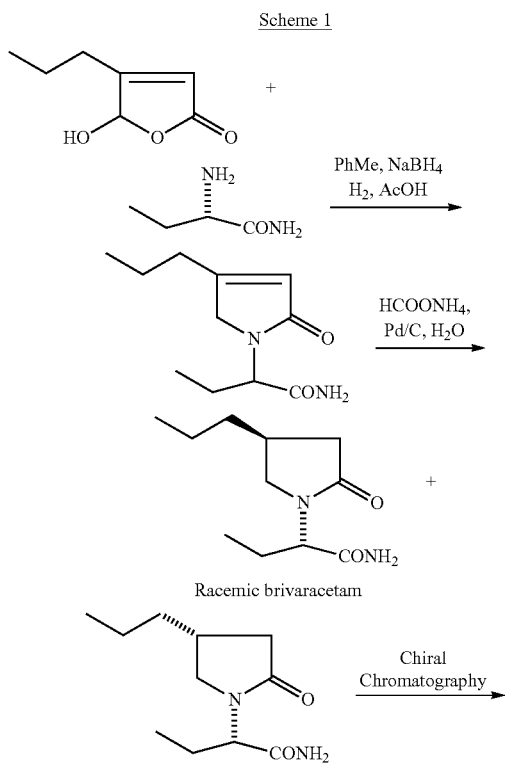

The U.S. Pat. No. 8,338,621, example 5, describes condensation of (R)-4-propyl-pyrrolidin-2-one, with (R)-2-bromobutyric acid to obtain (S)-2-[(S)4-propyl-2-oxopyrrolidin-1-yl] butyric acid having 95.9% (2S,4S) and 4.1% (2S,4R) isomers (Scheme 2). The acid thus obtained, on reaction with ammonia, followed by chiral chromatography gives Brivaracetam.

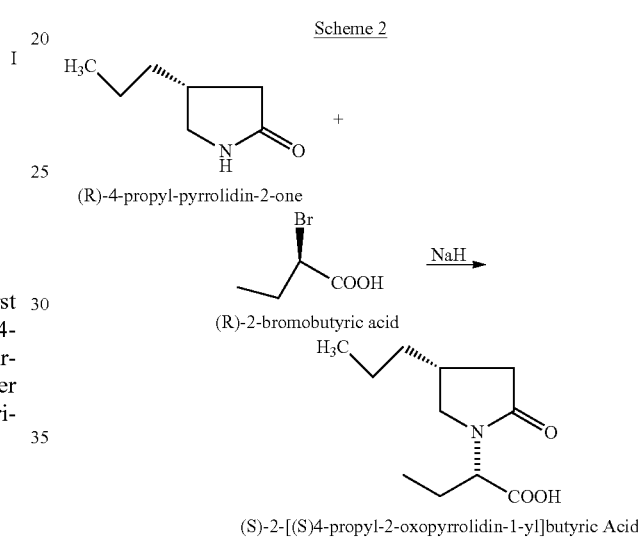

The U.S. Pat. No. 8,957,226 B2, example 3, describes the synthesis of Brivaracetam where (R)-4-propyl-pyrrolidin-2-one is condensed with racemic methyl ester of 2-bromobutyric acid using sodium hydride as a base in tetrahydrofuran resulting in (RS)-2-((2)-2-oxo-4-propylpyrrolidin-1-yl) butyric acid methyl ester followed by the reaction with ammonium hydroxide resulting in racemic Brivaracetam. The racemic mixture is resolved using chiral chromatography to obtain Brivaracetam (Scheme 3).

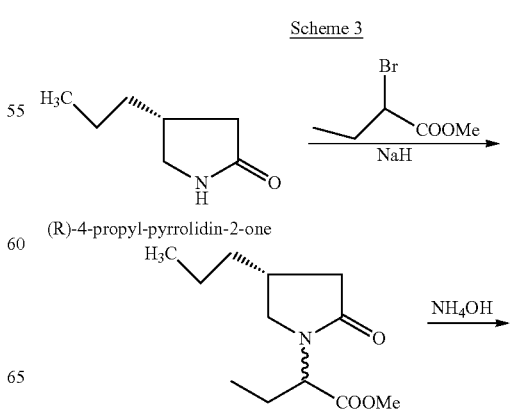

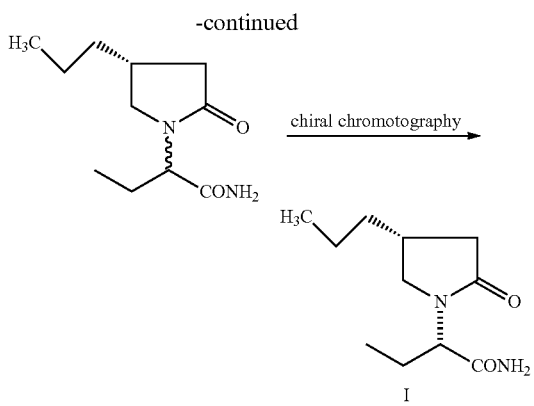

The above reported processes for obtaining enantiomerically pure Brivaracetam involves the use of chiral chromatography which is not suitable at industrial scale.

SUMMARY OF THE INVENTION

The objective of the present invention is to provide a process for the preparation of enantiomerically pure Brivaracetam without using chiral chromatography.

According to one aspect of the present invention, there is provided a process for the preparation of Brivaracetam which comprises the steps of (Scheme 4):
(i) converting the racemic (2RS)-2-[(4R)-2-oxo-4-propyl-pyrrolidin-1-yl] butyric acid methyl ester (II) into (2S)-2-[(4R)-2-oxo-4-propyl-pyrrolidin-1-yl] butyric acid (III) using protease from *Bacillus licheniformis*,
(ii) converting the free acid of formula (III) into amide to obtain Brivaracetam (I).

Another aspect of the present invention is to provide a process for the conversion of the compound (III) into Brivaracetam (I) which comprises reacting (III) with ethyl chloroformate and ammonia in the presence of a base.

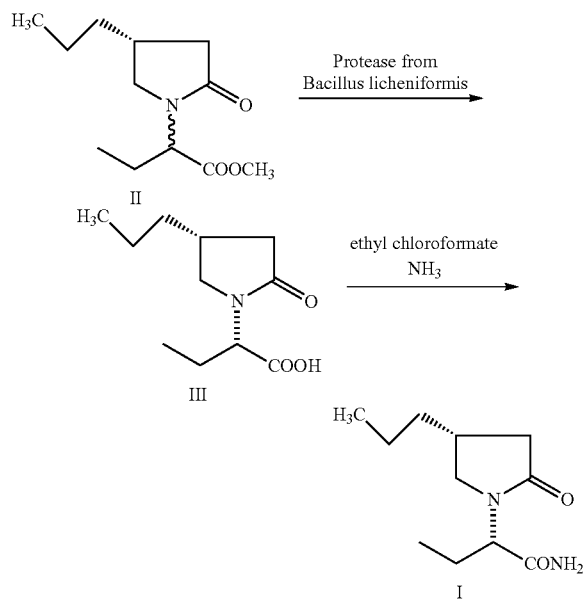

DETAILED DESCRIPTION OF THE INVENTION

The present invention provides a novel enzymatic process for the preparation of Brivaracetam which comprises the steps of:
(i) converting the racemic (2RS)-2-[(4R)-2-oxo-4-propyl-pyrrolidin-1-yl] butyric acid methyl ester (II) by reacting with protease from *Bacillus licheniformis* into (2S)-2-[(4R)-2-oxo-4-propyl-pyrrolidin-1-yl] butyric acid (III) (ii) converting the free acid of formula (III) into amide to obtain Brivaracetam (I).

The required starting compound, (2RS)-2-[(4R)-2-oxo-4-propyl-pyrrolidin-1-yl] butyric acid methyl ester (II) can be prepared by the method as described in the U.S. Pat. No. 8,338,621, example 5, by condensation of (R)-4-propyl-pyrrolidin-2-one, with (R, S)-2-bromobutyric acid, instead of (R)-2-bromobutyric acid, followed by esterification using methanol and sulphuric acid.

It is important to note that the chiral purity of (III) is subordinate to the chiral purity of (R)-4-propyl-pyrrolidin-2-one. Hence, to keep the presence of unwanted isomer (2RS)-2-[(4S)-2-oxo-4-propyl-pyrrolidin-1-yl] butyric acid methyl ester in the compound (II) within the limit, the (R)-4-propyl-pyrrolidin-2-one used must have high enantiomeric purity (>98%).

Initially, various commercially available esterase enzymes such as lipase from *Pseudomonas fluorescens*(EC. 3.1.1.34, from Amano) and lipase from *Candida antarctica* (Lipase B, EC. 3.1.1.3, from Novozymes) were studied. However, they both failed to hydrolyse the ester (II). Next, serine proteases belonging to the class EC. 3.4.21 were studied, as they exhibit promiscuous esterase activity, in addition to their amidase activity. It was gratifying to note that the commercially available protease from *Bacillus licheniformis*(alcalase) was able to hydrolyse the racemic ester (II) in a selective manner resulting in (2S)-2-[(4R)-2-oxo-4-propyl-pyrrolidin-1-yl] butyric acid (III) with high enantiomeric purity. Another protease, subtilisin Carlsberg (Bacterial alkaline protease, EC.3.4.21.62) also hydrolysed (II) in a selective manner, but the yields were lower compared to alcalase.

The reaction was carried out by stirring (2RS)-2-[(4R)-4-propyl-2-oxopyrrolidin-1-yl] butyric acid methyl ester (II) in phosphate buffer (0.2 M, 7.2 pH) at 27(±2)° C., to which alcalase (protease from *Bacillus licheniformis*, EC. 3.4.21.62, Sigma, Product Number: P4860, 2.58 U/g) was added and stirring continued for about 8 to 12 hours. Throughout the reaction pH was maintained by adding 10% ammonium hydroxide solution using pH Stat. Completion of the reaction was reflected when the consumption of ammonium hydroxide stopped. After the reaction, the reaction mixture was extracted with an organic solvent selected from the group consisting of n-hexanes, n-heptanes, and diisopropyl ether, to remove the unreacted compound (II). The aqueous layer was acidified to pH 2.0 using 5N HCl and extracted with an organic solvent selected from the group consisting of dichloromethane, ethyl acetate, and isopropyl acetate. The organic layer was washed with water and dried over anhydrous sodium sulphate. Concentration of the organic layer under reduced pressure results in (2S)-2-[(4R)-2-oxo-4-propylpyrrolidin-1-yl] butanoic acid (III) with high chemical and chiral purity.

Reaction time longer than about 12 hours results in lower chiral purity due to non-enzymatic hydrolysis. Shorter reaction time (<8 hours) results in lower yields. Below pH 7, poor yields were obtained and at above pH 8, lower chiral purity of the product was observed. The optimum reaction temperature is about 25-35° C. At 40-45° C. both yields and purity got decreased and at 10° C. lower yields were obtained. The optimum enzyme load was found to be 20% w/w. The reaction of the compound (III) with ammonia may be carried out in the presence of ethyl chloroformate which activates the carboxylic group through the formation of mixed anhydride. The reaction may be carried out in a suitable solvent such as dichloromethane at a temperature between −10° C. to −20° C. using gaseous ammonia in the presence of an organic base such as triethyl amine, or N-methyl morpholine. After the reaction, salts are removed by filtration. The organic filtrate was washed with a solution of potassium carbonate to remove the unreacted compound (III). After concentrating the organic layer, the residue obtained is slurried in isopropyl acetate. Filtering the solid results in brivaracetam (I) having high chiral purity.

The embodiments of the present invention are further described in the following examples, which are not intended in any way to limit the scope of the invention.

EXAMPLES

Chemical purity was determined using HPLC under the following conditions:
Column: Inertsil ODS 3V,250 X 4.6 mm, 5 μm
Mobile phase: Acetonitrile: Buffer (0.1% perchloric acid) (90:10 V/V); flow rate: 1.0 mL/min.
Column Temperature: 30° C.
Detection: 215 nm
Enantiomeric purity was determined using HPLC under the following conditions:
Column: CHIRALPAK-ADH 250 x 4.6 mm 5 μm
Mobile phase n-hexane: Isopropyl alcohol: Diethyl amine (85:15:0.1 ml), flow rate: 1.0 mL/min.
Column Temperature:30° C.
Detection: 215 nm Example 1: Preparation of (2RS)-2-[(4R)-4-propyl-2-oxopyrrolidin-1-yl] butyric acid methyl ester (II)

To a mixture of sodium hydride (60% oily dispersion,7.54 gm, 0.3144 mol) in 50 mL tetrahydrofuran was added a solution of (S)-4-propyl pyrrolidin-2-one (10.0 gm, 0.0786 mol) in 30 mL tetrahydrofuran at 0-5° C. To the mixture was added a solution of 2-bromo butanoic acid (15.75 gm, 0.094 mol) in 20 mL tetrahydrofuran. The reaction mixture was warmed and stirred at room temperature for 10-12 hours. The mixture was poured into crushed ice to decompose excess sodium hydride. Tetrahydrofuran was distilled under reduced pressure and the aqueous residue was adjusted to pH 2.0 at 0-5° C. using hydrochloric acid. The residue was extracted with isopropyl acetate (25 mLx3). The organic layer was concentrated to obtain (2RS)-2-[(4R)-4-propyl-2-oxopyrrolidin-1-yl] butyric as a colourless solid (15.8 gm, 94.2%).

The above acid (10 gm, 0.046 mol), was dissolved in 100 mL methanol. To this was added concentrated sulphuric acid (0.45 gm, 0.0045 mol) and maintained at room temperature for 12 hours. The solution was concentrated under reduced pressure. To the residue was added 50 mL cold water and extracted with dichloromethane (25mLx3). The dichloromethane solution was washed with saturated sodium bicarbonate solution followed by water. After drying over anhydrous sodium sulphate, the solution was concentrated under reduced pressure to obtain 9.2 gm of (2RS)-2-[(4R)-4-propyl-2-oxopyrrolidin-1-yl] butyric acid methyl ester (II) as an yellowish oil (Yield=86.38%, G.C: 99.4%).

Example 2. Preparation of (2S)-2-[(4R)-2-oxo-4-propylpyrrolidin-1-yl] butanoic acid (III)

To a solution of potassium phosphate buffer (120 mL, 0.2 M, pH 7.2) was added 12.0 gm (0.0528 mol) of (2RS)-2-[(4R)-4-propyl-2-oxopyrrolidin-1-yl] butyric acid methyl ester (II) and stirred at 27(±2) ° C. To the reaction mixture was added 2.4 gm alcalase (protease from *Bacillus licheniformis*, EC. 3.4.21.62, Sigma, Product Number: P4860, 2.58 U/g) and stirred for about 10 hours maintaining the pH at 7.2 using 10% ammonium hydroxide solution with the help of a pH Stat. The reaction mixture was extracted with n-hexanes to recover the unreacted starting material (unwanted isomer). The pH of the aqueous layer was adjusted to 2.0 using 5N HCl and extracted with isopropyl acetate. The organic layer was washed with water and dried over anhydrous sodium sulphate. Concentration of the organic layer under reduced pressure resulted in 4.83 gm of (2S)-2-[(4R)-2-oxo-4-propylpyrrolidin-1-yl] butanoic acid. Yield=80.5%, purity 99.3% (HPLC), Chiral purity: 99.4% (HPLC).

Example 3: Preparation of (2S)-2-[(4R)-2-oxo-4-propylpyrrolidin-1-yl] butanoic acid (III)

Experiment was conducted as described in Example 2, but at pH 7.8 instead of pH 7.2. Yield=76.3%, purity 99.1% (HPLC), Chiral purity: 98.9% (HPLC).

Example 4: Preparation of (2S)-2-[(4R)-2-oxo-4-propylpyrrolidin-1-yl] butanoic acid (III)

Experiment was conducted as described in Example 2, but at a temperature of 35(±2)° C., instead at 27(±2)° C. Yield=78.4%, purity 99.2% (HPLC), Chiral purity: 99.3% (HPLC).

Example 5 : Preparation of (2S)-2-[(4R)-2-oxo-4-propylpyrrolidin-1-yl] butanoic acid (III)

Experiment was conducted as described in Example 2, wherein the reaction was conducted for 8 hours. Yield=75%, purity 99.5% (HPLC), Chiral purity: 99.4% (HPLC).

Example 6: Preparation of Brivaracetam (I)

To a cooled solution of 10 gm (0.046 mol) of (2S)-2-((R)-2-oxo-4-propylpyrrolidin-1-yl) butanoic acid (III) and triethyl amine (7.1 gm, 0.07 mol) in 100 mL dichloromethane was added dropwise ethyl chloroformate 5.54 gm (0.05 mol) at −15° C. After stirring for 30 minutes, ammonia gas was passed, and the mixture was stirred for 2 hours at −15° C., and for 1 hour at 25-30° C. Salts were filtered and the filtrate was washed with a solution of potassium carbonate (10% solution, 50 mLx2) to remove unreacted (III). The organic layer was dried over anhydrous sodium sulphate and concentrated to obtain colourless solid. It was slurried in isopropyl acetate (15 mL) at 0-5° C. for 30minutes and filtered to obtain 8.79 gm of (I) as colourless solid (Yield=88%, HPLC: 99.6, Chiral HPLC: 99.8%).

We claim:
1. A process of preparing (2S)-2-[(4R)-2-oxo-4-propyl-pyrrolidin-1-yl] butanamide having the formula (I),

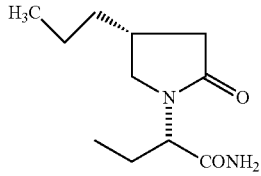

comprising:
(a) reacting (2RS)-2-[(4R)-2-oxo-4-propyl-pyrrolidin-1-yl] butyric acid methyl ester having the formula (II),

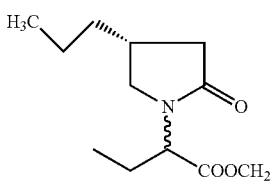

with an alcalase protease from *Bacillus licheniformis* in an aqueous solution;
(b) extracting the reaction mixture with an organic solvent selected from the group consisting of n-hexanes, n-heptanes, and diisopropyl ether, to remove unreacted compound of formula (II), and acidifying the aqueous layer using 5N hydrochloric acid.
(c) extracting the acidified layer from step (b), with an organic solvent selected from the group consisting of dichloromethane, ethyl acetate, and isopropyl acetate, to obtain (2S)-2-[ (4R)-2-oxo-4-propyl-pyrrolidin-1-yl] butyric acid of the formula (III), having >95% chiral purity; and

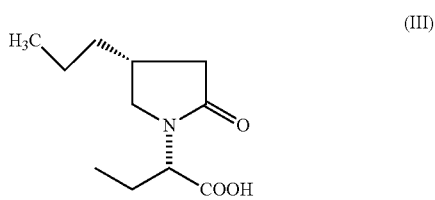

(d) reacting the compound of formula (III) with ammonia in dichloromethane, at a temperature of −10° C. to −20° C., in the presence of ethyl chloroformate and a base to obtain the butanamide having the formula (I).

2. The process of claim 1, wherein at step (a), the reaction is conducted at a pH between 7.0 and 7.8.

3. The process of claim 2, wherein, during the reaction, the pH is maintained by adding 5-10% solution of ammonium hydroxide.

4. The process of claim 1, wherein at step (a), the reaction is conducted at a temperature between 20° C. and 35° C.

* * * * *